(12) United States Patent
Carlone et al.

(10) Patent No.: US 8,983,573 B2
(45) Date of Patent: Mar. 17, 2015

(54) RADIATION THERAPY SYSTEM

(75) Inventors: Marco Carlone, Toronto (CA); B. Gino Fallone, Edmonton (CA); Brad Murray, Sherwood park (CA)

(73) Assignee: Alberta Health Services, Edmonton, Alberta (CA)

( * ) Notice: Subject to any disclaimer, the term of this patent is extended or adjusted under 35 U.S.C. 154(b) by 0 days.

(21) Appl. No.: 13/001,160

(22) PCT Filed: Jun. 25, 2009

(86) PCT No.: PCT/CA2009/000873
§ 371 (c)(1),
(2), (4) Date: May 13, 2011

(87) PCT Pub. No.: WO2009/155700
PCT Pub. Date: Dec. 30, 2009

(65) Prior Publication Data
US 2011/0218420 A1    Sep. 8, 2011

Related U.S. Application Data

(60) Provisional application No. 61/129,411, filed on Jun. 24, 2008.

(51) Int. Cl.
*A61B 5/055* (2006.01)
*G01R 33/48* (2006.01)
*A61N 5/10* (2006.01)
*G01R 33/38* (2006.01)

(52) U.S. Cl.
CPC .......... *G01R 33/4812* (2013.01); *A61N 5/1049* (2013.01); *A61N 2005/1055* (2013.01); *G01R 33/3806* (2013.01); *Y02E 10/38* (2013.01)

USPC ........... 600/411; 600/1; 600/422; 250/492.1; 250/492.3; 378/65

(58) Field of Classification Search
USPC ............... 600/1, 411, 422; 250/491.1, 492.1, 250/492.3; 378/65
See application file for complete search history.

(56) References Cited

U.S. PATENT DOCUMENTS

| | | | |
|---|---|---|---|
| 6,366,798 B2 | 4/2002 | Green | |
| 6,862,469 B2 | 3/2005 | Bucholz et al. | |
| 6,879,852 B1 * | 4/2005 | Mueller | 600/410 |

(Continued)

FOREIGN PATENT DOCUMENTS

| | | |
|---|---|---|
| WO | WO 99/32189 A1 | 7/1999 |
| WO | WO-99/32189 A1 | 7/1999 |
| WO | WO 2004/024235 A1 | 3/2004 |
| WO | WO 2006/136865 A1 | 12/2006 |
| WO | WO-2007/045076 A1 | 4/2007 |
| WO | WO 2007/045076 A1 | 4/2007 |

OTHER PUBLICATIONS

Bielajew, Alex F., et al.; "The effect of strong longitudinal magnetic fields on dose deposition from electron and photon beams"; Med. Phys. 20 (4); Jul./Aug. 1993; pp. 1171-1179.

(Continued)

*Primary Examiner* — Ruth S Smith
(74) *Attorney, Agent, or Firm* — Alston & Bird LLP

(57) ABSTRACT

A radiation therapy System comprises a magnetic resonance imaging (MRI) apparatus and a linear accelerator capable of generating a beam of radiation. The linear accelerator is immersed in and oriented with respect to the MRI magnetic field to expose the linear accelerator to magnetic force that directs particles therein along a central axis thereof.

12 Claims, 4 Drawing Sheets

(56) References Cited

U.S. PATENT DOCUMENTS

| | | | |
|---|---|---|---|
| 7,375,357 B2 | 5/2008 | Kaufman | |
| 7,960,710 B2* | 6/2011 | Kruip et al. | 250/492.3 |
| 2005/0197564 A1 | 9/2005 | Dempsey | |
| 2006/0267585 A1* | 11/2006 | Havens | 324/318 |
| 2008/0083871 A1* | 4/2008 | Cravens et al. | 250/252.1 |

OTHER PUBLICATIONS

Kirby, C., et al.; "Patient dosimetry for hybrid MRI-radiotherapy systems"; Med. Phys. 35 (3); Mar. 2008; pp. 1019-1027.

International Search Report and Written Opinion for International Application No. PCT/CA2009/000873, mailed Oct. 15, 2009.

Office Action for European Application No. 09 768 670.3 dated Jan. 16, 2013.

Australian Office Action for Application No. 2009261910, dated Aug. 15, 2012.

Communication Pursuant to Article 34(3) EPC for Application No. 09 768 670.3; dated Sep. 27, 2013.

Office Action for Chinese Application No. 200980124176.5; dated Jul. 25, 2013.

Office Action for Canadian Application No. 2,728,111; dated Dec. 9, 2013.

Supplemental European Search Report for Application No. EP 09 76 8670; dated Jun. 8, 2011.

* cited by examiner

RADIATION THERAPY SYSTEM

CROSS-REFERENCE TO RELATED APPLICATION

This application claims priority under 35 U.S.C. 119(e) from U.S. Provisional Patent Application Ser. No. 61/129,411 filed Jun. 24, 2008, the contents of which are entirely incorporated herein by reference.

FIELD OF THE INVENTION

The present invention relates generally to radiation therapy and in particular to a radiation therapy system in which a linear accelerator is immersed in and oriented with respect to the magnetic field of an MRI apparatus to expose the linear accelerator to magnetic force that directs electrons therein along a central axis thereof.

BACKGROUND OF THE INVENTION

Image guidance for radiation therapy is an active area of investigation and technology development. Current radiotherapy practice utilizes highly conformal radiation portals that are directed at a precisely defined target region. This target region consists of the Gross Tumour Volume (GTV), the Clinical Target Volume (CTV) and the Planning Target Volume (PTV). The GTV and CTV consist of gross tumour disease and the subclinical microscopic extension of the gross disease. During radiation treatments, these volumes must be irradiated at a sufficient dose in order to give an appropriate treatment to the patient. Because of the uncertainty in identifying this volume at the time of treatment, and due to unavoidable patient and tumour motion, an enlarged, the PTV is typically irradiated.

Because a volume that is larger than the biological extent of the disease is typically irradiated, there is an increased risk of normal tissue complications due to the unnecessary irradiation of healthy tissue. Thus, it is desirable to conform the radiation beam to the GTV and CTV only, and to provide an imaging method to assist in the placement of the radiation beam on this volume at the time of treatment. This technique is known as Image Guided Radiation Therapy (IGRT).

Commercially available techniques that are available for IGRT typically use x-ray or ultrasound imaging technology to produce planar x-ray, computed tomography, or 3D ultrasound images. Furthermore, fiducial markers can be used in conjunction with these imaging techniques to improve contrast. However, fiducial markers must be placed using an invasive technique, and are thus less desirable. IGRT techniques based or x-rays or ultrasound are not ideally suited to IGRT: x-rays suffer from low soft tissue contrast and are not ideally suited to imaging tumours; ultrasound cannot be utilized in all locations of the body. Further, x-ray based techniques use ionizing radiation and thus deposit supplemental dose to the patient. Finally, x-ray and ultrasound based IGRT techniques are difficult to integrate into a linear accelerator such that they can provide images in any imaging plane in real time at the same moment as the treatment occurs.

In order to overcome these difficulties, it has been proposed to integrate radiotherapy systems with a Magnetic Resonance Imaging (MRI) device. As is well known, MRI offers excellent imaging of soft tissues, and can image in any plane in real time.

An MRI functions by providing a homogeneous, and strong magnetic field that aligns the nuclear magnetic moments of target nuclei; hydrogen nuclei (protons) are the most common imaging target in MRI. In the presence of the magnetic field, the magnetic moments of the nuclei align with the homogeneous magnetic field and oscillate at a frequency determined by the field strength; this frequency is known as the Larmor frequency. This alignment can be perturbed using a radiofrequency (RF) pulse, such that the magnetization flips from the direction of the magnetic field ($B_0$ field) to a perpendicular direction, and thus exhibits transverse magnetization. When the nuclei reverts back to its original state, the transverse magnetic moment decays to zero, while the longitudinal magnetic moment increases to its original value. Different soft tissues exhibit different transverse and longitudinal relaxation times. A specific magnetic field strength is applied to a small sample of tissue utilizing gradient magnetic coils, and images of these soft tissues can be formed by generating a specific sequence of perturbing RF pulses and analyzing the signals that are emitted by the nuclei as they return to their original magnetization state after being perturbed by the first RF pulse.

A medical linear accelerator functions by using a cylindrical waveguide that is excited in a $TM_{010}$ mode such that the electric field lies upon the central axis of the waveguide. The phase velocity of the structure is controlled by introducing septa into the waveguide which form cavities. The septa have small holes at their centre to allow passage of an electron beam. Septa have the further advantage that they intensify the electric field at the center of the waveguide such that field gradients in the MeV/m range are available for RF input power that is in the MW range. Electrons are introduced into one end of the accelerating structure, and are then accelerated to MeV energies by the central electric field of the accelerating waveguide. These electrons are aimed at a high atomic number target, and the electronic energy is converted in high energy x-rays by the bremsstrahlung process. The waveguide is typically mounted on a C-arm gantry such the central axis of the waveguide is parallel to the ground. This waveguide rotates around a patient, which lies at the central axis of rotation. The medical accelerator utilizes a system employing a 270° bending magnet such that the radiation beam generated by the waveguide is focused at a point on the central axis of rotation known as the isocentre.

As is known, there are several significant technological challenges associated with the integration of a linear accelerator with an MRI device.

For example, if the linear accelerator is physically close to the MRI, the large magnetic field of the MRI magnet can affect the acceleration of electrons in the accelerating waveguide since electrons axe charged panicles, and are thus influenced by the Lorentz force, $F=q(v \times B)$, where $v \times B$ is the cross product between the electron velocity v, and the magnetic flux density B. If the direction of the electron motion is perpendicular to the magnetic field direction, the deflection of the electron's path will be a maximum, and it will very often result in electrons tending to collide with the side wall of the linear accelerator, which will stop the particle accelerating process.

A further challenge is due to the pulsed power nature of the linear accelerator. In order to supply sufficient RF power (on the order of Mega-Watts MWs) to the accelerating waveguide, medical linear accelerators operate in a pulsed power mode where high voltage is converted to pulsed power using a pulse forming network (PFN). The process of generating high voltage pulses involves sudden starting and stopping of large currents in the modulation process, and these in turn can give rise to radiofrequency emissions whose spectrum can overlap the Larmor frequency of the hydrogen nuclei within the imaging subject. This would thus interfere with the signals emitted by these nuclei as they relax, and would thus deteriorate the image forming process of the MRI.

A further challenge that exists when integrating an MRI with a medical linear accelerator involves the orientation of the MRI magnet with respect to the accelerating waveguide such that the waveguide can be directed at the patient without obstruction from the magnet.

A further challenge relates to the dose deposition pattern obtained when a patient is exposed to high energy x-ray used in radiotherapy in the presence of a strong magnetic field used far imaging by MRI. The dose deposited by the MRI is due to electrons scattered by the incoming photons by the photoelectric, Compton, or pair production processes. These electrons are charged particles, and are also subject to the Lorentz force. If the direction of the magnetic flux density is perpendicular to the incident direction of the x-ray beam, this produces perturbations to the dose deposition pattern that are significant, and increase in magnitude as the magnetic flux density increases.

U.S. Pat. No. 6,365,798 to Green discloses a method of mounting an open, bi-planar magnet on a conventional C-arm medical linear accelerator. The design of the linear accelerator is not changed from that built by the patent assignee (Varian), and much of the patent describes methods of retrofitting an MRI magnet to an existing design of linear accelerator. Several configurations of an MRI magnet are described. For example, the magnet can be mounted independently of the C-arm accelerator, and thus remain stationary. In this configuration the magnet has a wide enough opening to allow irradiation from several angles. Alternatively, the MRI magnet is mounted on the C-arm gantry, and rotates with the gantry to provide rotational therapy. Green relies on the MRI magnet being small enough to be able to be added to an existing medical accelerator manufactured by Varian Medical Systems.

Further, according to Green the MRI magnet is positioned so that the radiation beam itself is parallel or perpendicular to the direction of the main magnetic field. Several magnet orientations are described, and include coils with a central opening (for passage of the patient or the radiation beam) or no central opening.

To avoid interference between electron acceleration or the linear accelerator's 270° bending magnet and the MRI, Green suggests a low magnetic field that is only just sufficient to provide the lowest quality image to align a beam with a specified region of tissue. As well, active shielding methods to reduce the magnetic field from the MRI magnet at the accelerating waveguide of the medical linear accelerator are employed. Green does not contemplate a solution to RF interference problems described above.

The Green document also suggests a mechanism whereby an x-ray beam would cause spectral changes in the NMR spectra of the tissues being irradiated, and further describes a method that would image the region of tissue being irradiated based on the suggested NMR spectral changes.

PCT Patent Application Publication No. WO 2004/024235 to Lagendijk discloses a cylindrical, solenoid shaped MRI magnet that is combined with a linear accelerator that is mounted perpendicular to this magnet (at its mid-point) and points to the central axis of the magnet. The patient lies on the central axis of the cylindrical magnet, with the magnetic field in the cranial-caudal direction. The radiation beam is perpendicular to the direction of magnetic field. The magnet is designed with active shielding such that the magnetic field where the accelerating waveguide is located is reduced to a low value. The radiation beam must penetrate the solenoidal magnet to reach the patient located inside the solenoid, and is thus attenuated by the magnet. Filters are described to compensate for the effects of the solenoidal magnet on the quality of the x-ray beam. As well an embodiment whereby the solenoidal magnet is split such that an unattenuated x-ray beam reaches the patient is also described. No solutions to the RF interference, or perturbation of the dose distribution by the $B_0$ field are described.

U.S. Pat. No. 6,862,469 to Bucholz et al, discloses a method to combine a proton beam with an MRI system. This invention is indirectly related to the current disclosure since it relates to proton therapy, and does not discuss methods of bringing a medical linear accelerator close to an MRI magnet. This disclosure describes a photon beam that impinges through an aperture of an MRI magnet in the same direction as the $B_0$ field, and is thus not deflected by the $B_0$ field since the vector product v×B is 0 in this case. A limitation of this disclosure is the small aperture size in the magnet.

Specific discussion about interference between the manufacture of the proton beam MRI operation is not discussed. Typically, in proton irradiators, the proton beam is accelerated to the desired energy far from the patient. It is thus implied that the proton acceleration process does not produce magnetic interference with the MRI.

A significant part of the Bucholz et al. disclosure relates to feedback methods whereby the MRI imaging information is used to position the proton beam at the suitable position on the patient.

Bucholz et al. describe a system where the patient is rotated is for rotational therapy; however gantry rotation of the proton beam is briefly mentioned. For a rotating gantry, Bucholz describes a stationary MRI magnet where beam access through the magnet gap is proposed.

Bucholz et al. further briefly mention other magnetic and RF interference, and suggests that shielding methods ear be used to remove these, if needed.

PCT Patent Application Publication No. WO 2006/136865 to Kruip et al. discloses a MRI system that can be combined with proton therapy. A sophisticated magnet design is described that allows the proton beam to be in the same direction as the $B_0$ field of the MRI, but with a large opening that would allow for translation of the proton beam. The magnet design is complicated, and involves non-circular and complex coils. As in Bucholz et al., the proton source is far from the magnet, and the two devices are assumed not to interfere with each other magnetically. Furthermore, no discussion of rotation therapy is described.

U.S. Patent Application Publication No. 2005/0197564 to Dempsey discloses a method of delivering radiotherapy using a radionuclide as the source of ionizing radiation in combination with an open solenoid MRI. The patient is place in the bore of the MRI magnet such that the magnetic field is parallel to cranial-caudal direction. The radionuclide used is $^{60}Co$ and it is placed such the patient is irradiated through the opening of the MRI solenoid, and so the magnetic field is perpendicular to the direction of the x-ray beam. $^{60}Co$ is radioactive, and emits photons with a mean energy of 1.25 MeV.

In the Dempsey design, no accelerating waveguide is used and so the problems of an electron beam deflection in the accelerating waveguide by the $B_0$ field of the MRI are not encountered. RF interference between a medical linear accelerator and an MRI are also avoided since $^{60}Co$ does not use a PFN. However, this method introduces a new problem in that $^{60}C$ is ferromagnetic, and will thus introduce inhomogeneities in the $B_0$ field of the MRI. When the $^{60}Co$ source is rotated, these inhomogeneities will degrade the MRI image quality, which necessitates the use of novel techniques to recover the image quality. As well, $^{60}Co$ has a finite dose rate for a given source activity, which reduces in time due to the half life of $^{60}$Co. This dose rate is generally lower than that of a medical linear accelerator and is thus undesirable. As well, $^{60}$Co source size is large enough such that the focal point of the radiation source is larger than that of a medical linear accelerator. This reduces the x-ray beam quality of the $^{60}$Co source as compared to that of the medical linear accelerator.

Dempsey describes in some detail the perturbation effects on the dose distribution in the patient due to the magnetic field. He suggests that at 1.5 T, these perturbations are significant for perpendicular irradiation, but are considerably reduced, if not eliminated, when a low field MRI, such as 0.3 T, is used in perpendicular irradiation.

Dempsey also describes the use of alternate irradiation sources such as protons or neutrons.

PCT Patent Application Publication No WO 2007/045076 to Fallone et al., assigned to the assignee of the present application, and the contents of which are incorporated herein by reference, describes a medical linear accelerator that is combined with a bi-planar permanent magnet suitable for MRI.

While the documents described above provide various advancements, there are technological problems that are yet to be resolved. For example, several of the configurations described above propose a reliance on the use of magnetic shielding, or shimming. Such shielding is strategically placed on or around the system to mitigate the magnetic effect of the MRI on the linear accelerator as or to compensate for the effect of the ferromagnetic $^{60}$Co on the MRI. As a result of this reliance on magnetic shielding/shimming, these systems tend to be designed so as to provide as large a distance as possible between the MRI and linear accelerator or $^{60}$Co source. Unfortunately, increasing the distance between the MRI and linear accelerator lowers the photon dose rate seen at the MRI isocentre. As a result, the treatment time for providing necessary dosage is prolonged. Another significant drawback to the larger distance required between the linear accelerator and the isocentre is the according increase in the physical size of the combined MRI-linear accelerator. Such increases in size lead to difficulties in ensuring integrated MRI-linac devices can be installed in standard-size radiation therapy suites. As would be understood, a configuration that relies far less or not at all on magnetic shielding/shimming for reducing magnetic interference would pose fewer restrictions on the relative placement of the linac and the MRI. As a result, such a configuration would enable size reduction and dose rate increases without undesirable magnetic interference.

A second difficulty that is common to the above is that these produce dose distributions in the patient that are perturbed from the case where there is no magnetic field. This perturbation is due to the Lorentz force on the scattered electrons that originate when photons interact with the biological material of the patient. One of more of the above proposals use a device arrangement where the photon beam is perpendicular to the $B_0$ field of the MRI imager, and so in this case the Lorentz force on the scattered electrons is greatest. A device where the $B_0$ field was parallel to the direction of the photon beam would produce scattered electrons of which a great majority have a small angle of travel with that of the $B_D$ field, and would thus have a minimum Lorentz force on the scattered electrons. This will produce only a small perturbation to the dose distribution received by the patient. This effect has been studied, and is described by Bielajew, Med. Phys, vol 20, no. 4, pp 1171-1179 (1993).

The above-described patent to Green however, suggests an embodiment where the $B_0$ field of the MRI and the direction of the x-ray beam are parallel. A defining feature of disclosure Green, however, is that it uses a standard linear accelerator configuration where the accelerating waveguide is mounted on a C-arm gantry, and the accelerating waveguide is parallel to the floor, and rotates about an axis that is also parallel to the floor. Further, the layout of the MRI and accelerating waveguide described in Green is such that the linear accelerator uses a 270° betiding magnet to direct the photon beam toward the MRI. While contemplated, it would be understood by the skilled worker that such an embodiment is, however, highly unpractical. For example, an MRI that produces images of human subjects with a field of view that is large enough and has sufficient contrast to be useful in image guided radiotherapy is far larger than those that can fit directly under a standard linear accelerator as is suggested by Green. This is simply because the size of the MRI magnet is strongly related to the desired field of view size, and contrast is directly related to magnetic field strength. In other words, systems built according to the proportions shown in the Figures of Green would simply not be capable of producing images useful for guiding radiotherapy because it could not support magnets required to do so.

A further difficulty with Green is that it clearly relies on a low magnetic field strength to reduce magnetic interference between the MRI and linear accelerator. Further, Green suggests methods whereby NMR spectral techniques are used to visualize a radiation beam. However, those skilled in the art, knowing that the magnetic field strength is a limiting factor when producing high contrast imaging, would immediately recognize that one cannot rely on a low magnetic field to produce MRI images that are in arty way suitable for guiding radiotherapy. Further, it is well known that NMR spectroscopy functions well only at high magnetic field strengths.

It is therefore an object of the invention to at least mitigate the disadvantages encountered when integrating a linear accelerator and an MRI for image guided radiotherapy.

SUMMARY OF THE INVENTION

In accordance with an aspect, there is provided a radiation therapy system comprising:

a magnetic resonance imaging (MRI) apparatus; and a linear accelerator capable of generating a beam of radiation, the linear accelerator immersed in and oriented with respect to the MRI magnetic field to expose the linear accelerator to magnetic force that directs electrons therein along a central axis thereof.

In accordance with another aspect, there is provided a radiation therapy system comprising:

a magnetic resonance imaging (MRI) apparatus; and a linear accelerator capable of generating a beam of radiation, the linear accelerator immersed in and oriented with respect to the MRI magnetic field to expose the linear accelerator to magnetic force that focuses the electron beam therein.

The above-described radiation therapy system is advantageous particularly because the linear accelerator is positioned so as to be close to the MRI apparatus but not necessarily require magnetic shielding to limit the interference by the MRI magnet with the linear accelerator. Thus, design considerations for limiting the interference are reduced.

A further advantage of the design shown in this disclosure is that, for a practical system the magnetic flux density of the MRI magnet that can be combined with the linear accelerator can be relatively high. This is simply because the direction of electron travel in the linear accelerator is always parallel to the direction of the magnetic field. Thus, the Lorentz force on the electrons is close to or is equal to zero in this case, and no deflections of the electron trajectory are produced by the MRI magnetic field. Thus, if higher magnetic field strengths are required to improve the MRI image quality, the present disclosure can still be used to combine the MRI magnet and the linear accelerator.

A further advantage of the design shown in this disclosure is that the perturbation of the dose distribution in a patient is more desirable. In some prior proposals, the direction of the x-ray beam is perpendicular to the MICE magnet $B_0$ field. In such cases, the patient dose distribution is perturbed in an undesirable manner, and it can produce considerable hot or cold regions of dose. This effect has been described, for example, in Kirkby et al, Med. Phys. Vol 35, no. 3, pp. 1019-1027, (2008). The effect is directly due to the orientation of the x-ray beam and the direction of the MRI $B_0$ field, and cannot be removed. The effect intensifies at higher magnetic field strengths, and could limit the usefulness of the combined MRI-linear accelerator. However, as described in Bielajew (Med. Phys, vol 20, no. 4, pp 1171-1179 (1993)), when the x-ray beam is in the same direction as an external B field, the lateral electron scatter is reduced. On the central axis of a large field size, Bielajew showed that there is no change to the dose distribution as compared to the zero B field case. On a lateral profile, there will be a change to the dose distribution, since there is reduced lateral electron scattered due to the focusing effect of the Lorentz force. This change results in a sharper dose drop off in the penumbra region, and is thus beneficial in radiotherapy. Thus the dose distribution for the MRI-Linear accelerator system described here will have superior qualities to those in previously disclosed systems.

Another advantage provided is that due to the focusing of the particles, the dose distribution has a sharper dose drop off in the penumbra region, and thus exhibits improved beam sharpness at the beam edges.

A further advantage of the design shown in this disclosure is that it allows for a more compact size since the linear accelerator can be placed closer to the MRI magnet isocentre without any added complexity of magnetic shielding. This is a significant advantage since the practical usefulness of the device may otherwise be limited by its size. Firstly, the x-ray dose rate at isocenter is inversely proportional to the square of the distance from the linear accelerator target, and so an increased distance between the MRI and the linear accelerator means a dose rate reduction proportional to 1 divided by the square of the distance. Secondly, a combined MRI-linear accelerator that is too large to fit into a standard radiotherapy suite may be technologically feasible but commercially impractical since hospitals may not be able to modify available room dimensions within existing radiotherapy departments. A compact device which can be fitted into an existing suite will be less expensive to install and operate than a larger device which requires a new facility to be built, and thus offers economical and commercial advantages.

A further advantage of the design shown in this disclosure is that it allows radiotherapy treatments using an electron beam as well as a photon beam. For example, electron therapy is obtained simply by removing the high Z target from the exit of the accelerating waveguide, and instead using the electron beam directly for cancer therapy. In the present disclosure, the direction of electron motion is parallel to the magnetic field on the central axis, and so the electron trajectory will not be subject to a Lorentz force. Away from the central axis there will be a small Lorentz force on the electron motion. This force will cause a spiraling motion of the electron path about the direction of the magnetic field with a radius that is proportional to the electron's transverse momentum, and inversely proportional to the magnetic field strength. However, this motion will preserve the electron's longitudinal momentum, and thus it will not prevent the electron beam from reaching the patient. While one consideration is that such spiraling electron motion could cause synchrotron radiation, it has been shown by Bielajew (Med. Phys, vol 20, no. 4, pp 1171-1179 (1993)) that, at magnetic field strengths relevant to MRI and electron energies relevant to radiotherapy, such effects are minimal and have little, if any, detrimental consequences.

A further advantage of this of the design shown in this disclosure is that the calculation of dose in the patient is facilitated. In radiotherapy, the radiation dose is calculated by performing a convolution of the photon impulse function. This impulse function is the response of a primary photon at a single point, and is also known as a dose spread kernel. The dose spread kernel represents the spreading of the energy released during a photon interaction. The spreading is due to the subsequent random photon and electron interactions. As described by Bielajew (Med. Phys, vol 20, no. 4, pp 1171-1179 (1993)), the spreading of the electronic component of the dose spread function will be reduced in the presence of a parallel magnetic field, and will thus be physically smaller. Dosimetric computations due to a smaller dose spread kernel are easier to execute since the convolution required for accurate calculations will be less complex, and thus dose computations will be simplified in this case.

BRIEF DESCRIPTION OF THE DRAWINGS

Embodiments will now be described more fully with reference to the accompanying drawings in which.

DETAILED DESCRIPTION OF THE EMBODIMENTS

The present disclosure describes a device which addresses one or more of the problems set out above. In order to reduce the degree to which electrons stray from the central axis of the accelerating waveguide, and to thereby focus electrons on the accelerator's target, a linear accelerator can be immersed in a magnetic field that is parallel to the direction of electron travel in the accelerating waveguide, and advantageously and surprisingly the magnetic field can be provided by the MRI magnet itself.

Figure 1:
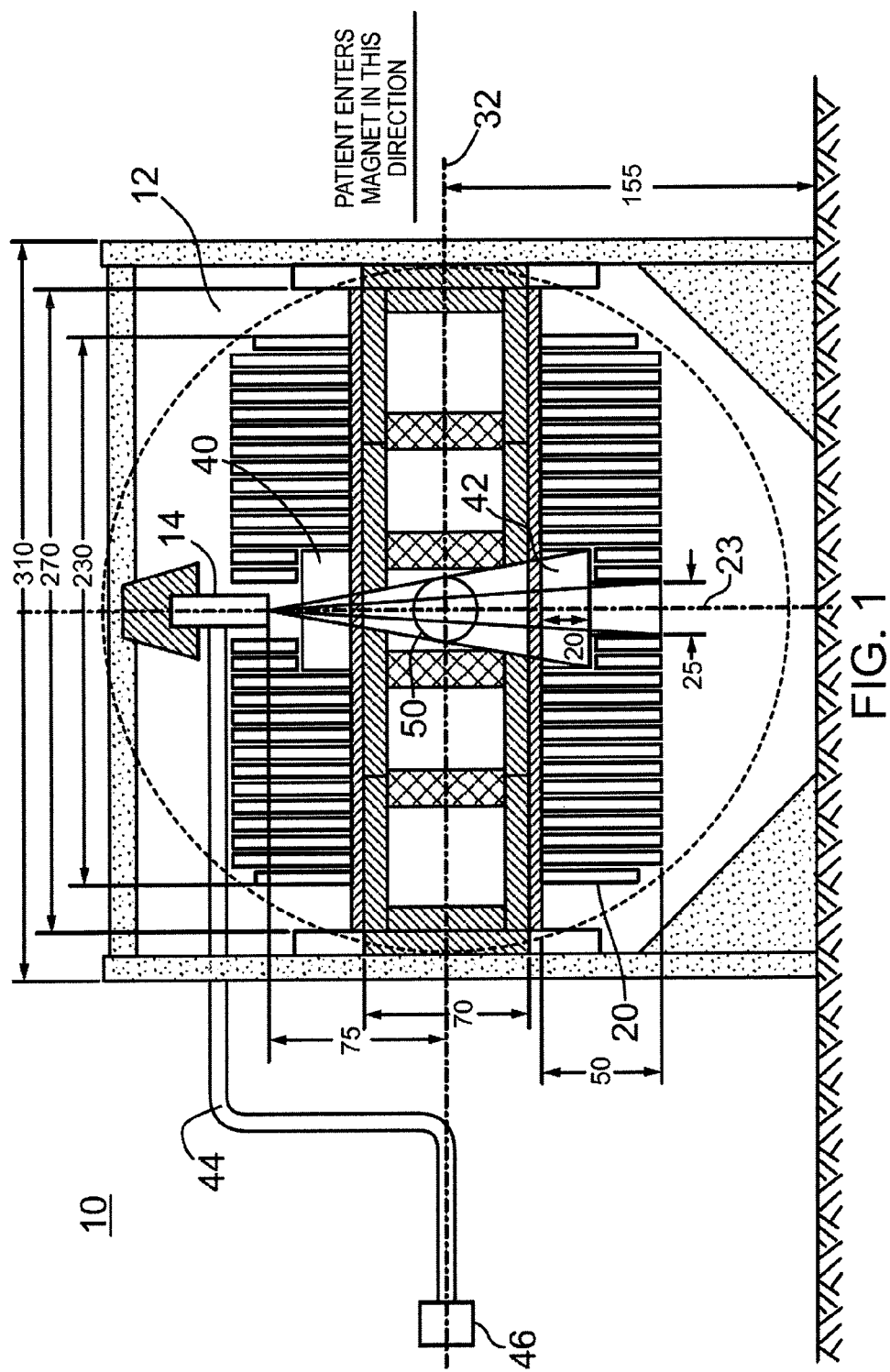
FIG. 1 is a side view of a radiation therapy system, according to an embodiment.

FIG. 1 is a side view of a radiation therapy system 10 according to an embodiment, that can fit entirely within a room that is three (3) meters in height. Radiation therapy system 10 comprises an open-bore, 0.2 Tesla MRI assembly 12 integrated with a standard S-band standing wave 6 MV linear accelerator 14. Radiation therapy system 10 is configured to provide a 30 cm diameter imaging volume 50, and comprises two sets of fourteen (14) circular coils 20 of different diameters that are concentrically positioned about a common central axis 23. The sets are in a fixed spaced relationship thereby to provide a space therebetween for entry of a patient. In this embodiment, the smallest of the circular coils 20 has an inner diameter of 25 centimeters, which is sufficient for receiving the linear accelerator 14. The largest of the circular coils 20 has a diameter of 230 centimeters. The magnet cylinder thicknesses are five (5) centimeters, and there is a 2.5 centimeter separation between coils 20. This separation is provided to enable connection to the support structure, and the interspersing of coolant such as water or a cryogenic coolant. As can be seen in FIG. 1, the inner two cylinders are shorter in order to accommodate the dimensions of a multi-leaf collimator (MLC) 40 for beam shaping, and a beam stop 42.

In FIG. 1, the patient enters the system 10 from the right hand side, and lies horizontally between the two sets of coils 20. The radiation therapy system 10 rotates about a horizontal axis 32 that is aligned with the cranial-caudal axis of the patient. The gap between inward facing surfaces of the two sets of coils 20 is 80 cm. This gap dimension accommodates two five (5) centimeter stainless steel plates 34 to be used to anchor the sets of coils 20, while permitting a 70 centimeter space between the sets of coils 20. The 70 centimeters space is sufficient to accommodate the addition of gradient magnets (not shown), while still allowing enough room to rotate the entire two sets of coils 20 around the patient.

Figure 2:
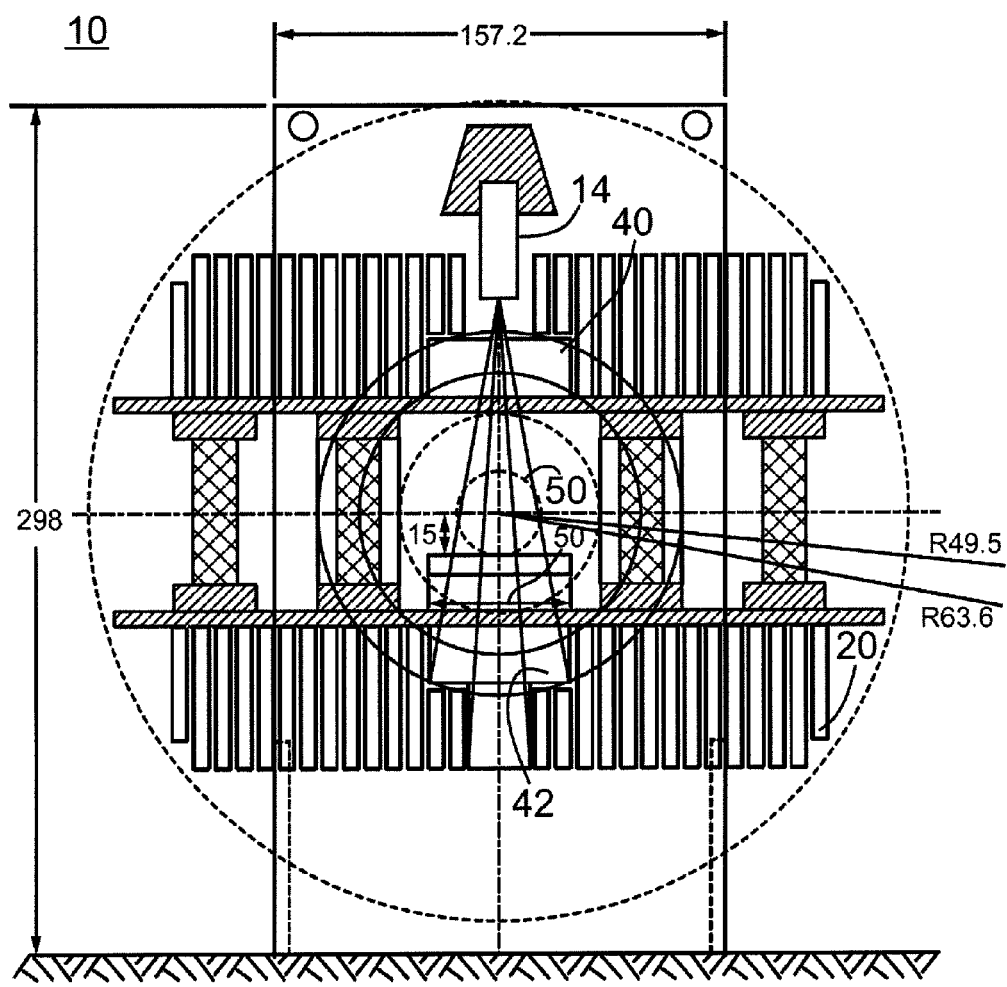
FIG. 2 is a front view of the radiation therapy system of FIG. 1.

A front view of the radiation therapy system 10 is shown in FIG. 2. In this view, the axis of rotation 32 is perpendicular to the page, and the patient enters the system by going in a direction that is into the page. A gantry ring supporting the system 10 is clearly seen in this view, as are support posts to give the assembly the required stiffness so as not to sag or warp when rotating.

Figure 3:
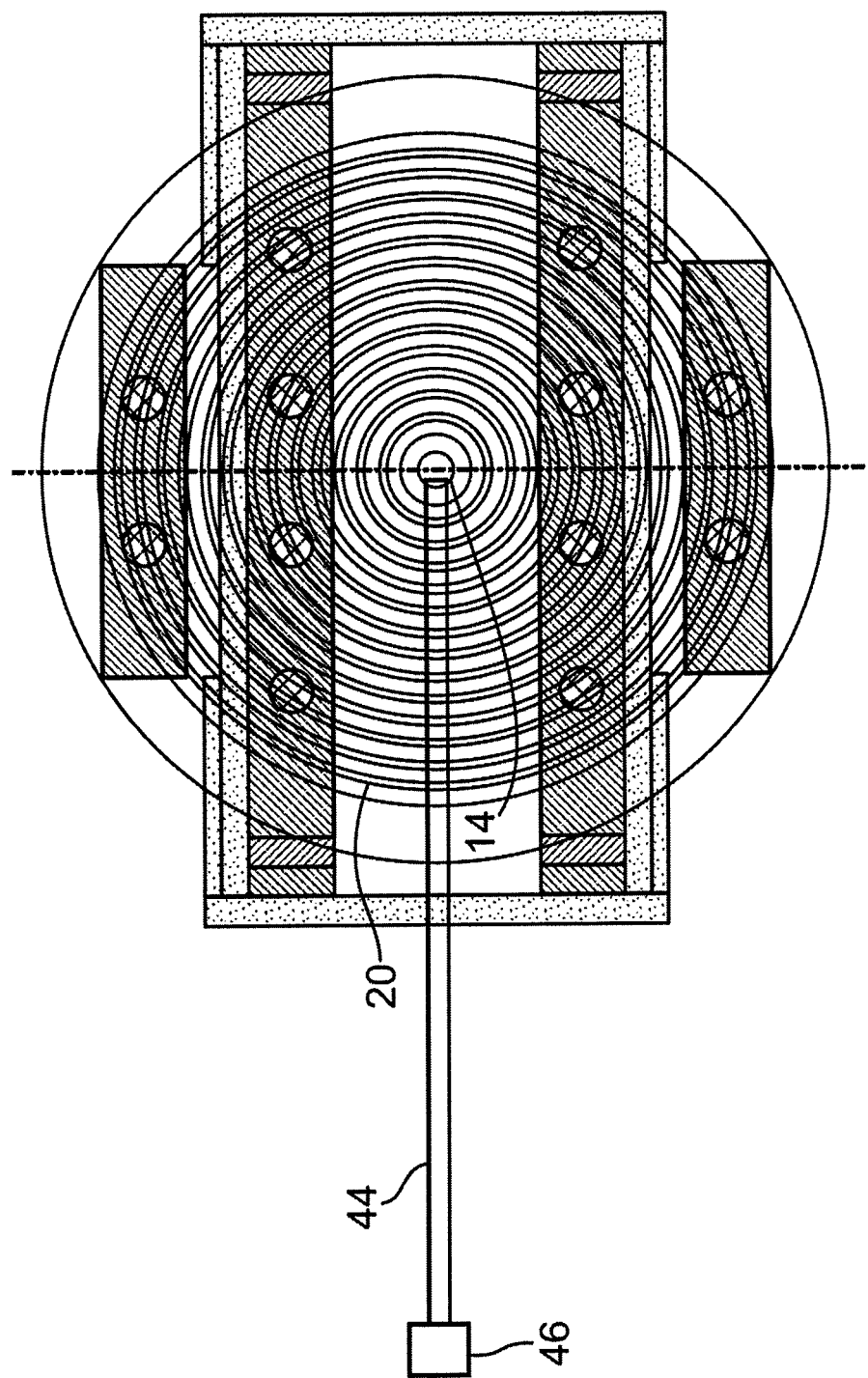
FIG. 3 is a top view of the radiation therapy system of FIG. 1.

A top view of the radiation therapy system 10 is shown in FIG. 3. In this view, the concentric magnet coils are clearly displayed, showing the linear accelerator positioned along the central axis 23.

Advantageously, the radiation therapy system 10 rotates as a unit about horizontal axis 32. The transmission RF waveguide 44 that is operably connected to the linear accelerator 14 is, in this embodiment, of type WR 284. The transmission RF waveguide 44 goes to a rotary joint 46 that rotates about the horizontal axis 32. Rotary joint 46 in turn provides coupling to a RF power supply that is, in this embodiment, located remote from the radiation therapy system 10. With this configuration, the RF power supply does not rotate.

Advantageously, the axis of particle travel within the linear accelerator 14 is also coincident with central axis 23. In this embodiment, linear accelerator 14 is positioned along central axis 23 partly within the 25 centimeter hole that is formed by the smallest of the circular coils 20, so as to provide a linear accelerator isocentre to target distance of 75 centimeters, which permits application of a high dose rate during treatment. In this position, linear accelerator 14 is immersed in and oriented with respect to the magnetic field produced by the MRI coils 20 to expose the linear accelerator 14 to magnetic force that directs (or "focuses") particles therein along the central axis 23 of the linear accelerator 14.

The mechanism of focusing is due to the presence of both longitudinal and radial magnetic fields at the central axis 23 at which the linear accelerator 14 has been positioned. Particles that enter the linear accelerator 14 away from its central axis 23 will experience a Lorentz force in the asimuthal direction due to the radial magnetic field of the MRI magnets. The resulting angular motion of the particles will then cause an inward radial Lorentz force due to interaction with the longitudinal magnetic field of the MRI magnets. The net result is a confinement of the particles to the central axis 23 of the linear accelerator 14. Thus, this configuration provides Lorentz force that assists the linear accelerator 14 by redirecting any stray particles back to the central axis 23 of the linear accelerator 14.

It would be understood that positioning of the linear accelerator 14 as described above places the linear accelerator within a region where the magnetic field has a reasonable level of homogeneity. This positioning thereby ensures a radial magnetic field that is advantageous for focusing of the particle beam within the linear accelerator 14.

While due to their use of RF fields for providing particle focusing, some modern standing wave linear accelerators 14 do not necessarily require additional focusing as described above, the positioning of the linear accelerator 14 as described above providing supplemental focusing will not harm the accelerator functionality, and will of course provide the compactness, perturbation-reduction, and increased dose rate advantages that have been described above. Furthermore, augmented performance of the linear accelerator 14 may result due to any additional particle focusing provided by the advantageous placement of the linear accelerator 14 relative to the MRI magnetic field. Such additional focusing would serve to reduce the beam spot size, among other things, thereby increasing the accuracy of the radiation therapy.

As an example, the Varian 2100 and 2300 series medical accelerators utilize a standing wave accelerating structure and also a waveguide focusing magnetic coil. Thus, this type of focusing magnetic field can be applied to any linear accelerator, and can be exploited to combine a linear accelerator with an MRI.

Figure 4A:
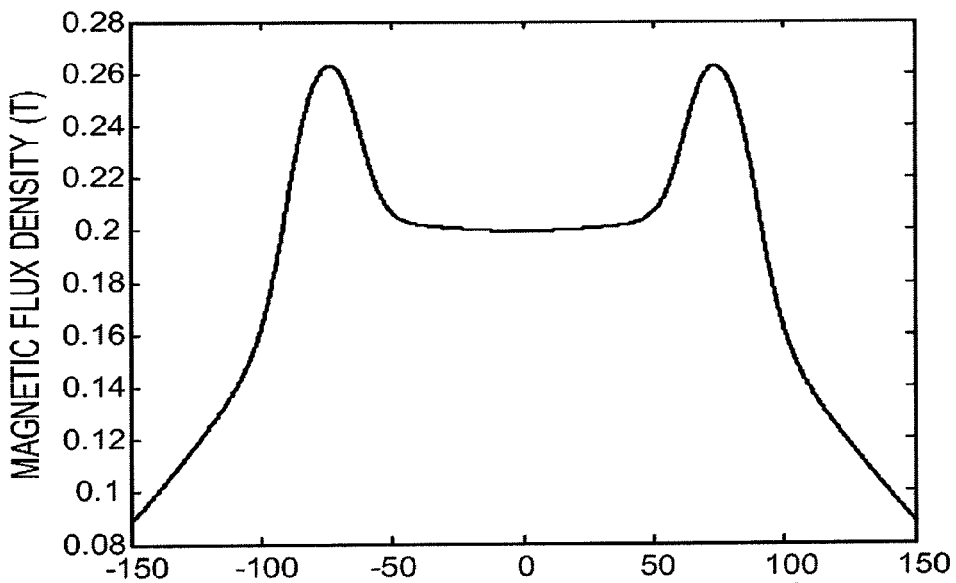
FIGS. 4a and 4b show two plots of magnetic flux density versus position for two different parameterizations of coil configurations of the radiation therapy system of FIG. 1.
Figure 4B:
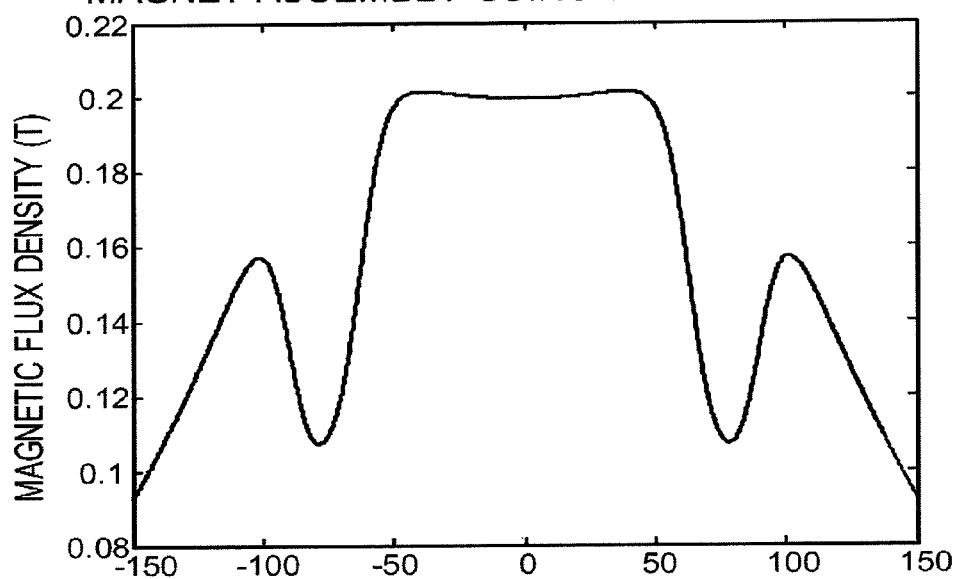

An example of a selected set of performance parameters is given in Tables 1 and 2, and the resulting central axis field plot in FIG. 4.

Table 1 shows parameters representing the coils 20 for radiation therapy system 10, where the coils 20 produce a somewhat uniform magnetic field in a 30 cm sphere-shaped imaging volume at the magnet isocentre, with about a 71 ppm nonuniformity. In this embodiment, the gauge of the copper wire for the coils 20 is 18 AWG; the total coil weight is 17,363 kilograms; and the total power dissipated is 1207 kW.

TABLE 1

| coil # | current (A) | resistance (Ω) | voltage (kV) | power (kW) | weight (kg) | Number of turns |
|---|---|---|---|---|---|---|
| 1 | 4.231 | 279.6 | 1.183 | 5.006 | 84.1 | 12173 |
| 2 | −2.919 | 419.4 | −1.224 | 3.573 | 126.2 | 12173 |
| 3 | 0.648 | 1016.8 | 0.659 | 0.427 | 305.2 | 22090 |
| 4 | −1.657 | 1271.0 | −2.107 | 3.492 | 381.6 | 22090 |
| 5 | 2.928 | 1525.3 | 4.465 | 13.073 | 457.9 | 22090 |
| 6 | −1.399 | 1779.5 | −2.489 | 3.481 | 534.2 | 22090 |
| 7 | 0.848 | 2033.7 | 1.724 | 1.462 | 610.5 | 22090 |
| 8 | 0.185 | 2287.9 | 0.423 | 0.078 | 686.9 | 22090 |
| 9 | −5.344 | 2542.1 | −13.586 | 72.606 | 763.2 | 22090 |
| 10 | −2.551 | 2796.3 | −7.133 | 18.193 | 839.5 | 22090 |
| 11 | 7.355 | 3050.5 | 22.437 | 165.032 | 915.8 | 22090 |
| 12 | 0.349 | 3304.7 | 1.153 | 0.402 | 992.2 | 22090 |
| 13 | 3.147 | 3558.9 | 11.201 | 35.255 | 1068.5 | 22090 |
| 14 | 9.599 | 3050.5 | 29.281 | 281.066 | 915.9 | 17672 |

Table 2 shows parameters representing the coils 20 for radiation therapy system 10, where the coils 20 produce an acceptably homogenous magnetic field in a 30 cm sphere-shaped imaging volume at the magnet isocentre, with about a 80 ppm nonhomoegenity. In this embodiment, the gauge of the copper wire for the coils 20 is 8 AWG; the total coil weight is 18,093 kilograms; and the total power dissipated is 1486 kiloWatts (kW).

TABLE 2

| coil # | current (A) | resistance (Ω) | voltage (kV) | power (kW) | weight (kg) | Number of turns |
|---|---|---|---|---|---|---|
| 1 | −56.548 | 2.845 | −0.161 | 9.10 | 87.31 | 1245 |
| 2 | 51.683 | 4.267 | 0.221 | 11.40 | 131.03 | 1245 |
| 3 | −1.813 | 10.345 | −0.019 | 0.03 | 317.92 | 2265 |
| 4 | −2.999 | 12.932 | −0.039 | 0.12 | 397.47 | 2265 |
| 5 | 15.246 | 15.518 | 0.237 | 3.61 | 477.01 | 2265 |
| 6 | −13.339 | 18.104 | −0.241 | 3.22 | 556.56 | 2265 |
| 7 | 24.029 | 20.690 | 0.497 | 11.95 | 636.10 | 2265 |
| 8 | −43.366 | 23.277 | −1.009 | 43.77 | 715.64 | 2265 |
| 9 | −68.877 | 25.863 | −1.781 | 122.70 | 795.19 | 2265 |
| 10 | 44.061 | 28.449 | 1.253 | 55.23 | 874.73 | 2265 |
| 11 | 94.814 | 31.036 | 2.943 | 279.00 | 954.28 | 2265 |
| 12 | −21.832 | 33.622 | −0.734 | 16.03 | 1033.82 | 2265 |
| 13 | 67.934 | 36.208 | 2.460 | 167.10 | 1113.36 | 2265 |
| 14 | 25.124 | 31.036 | 0.780 | 19.59 | 955.91 | 1815 |

FIG. 4 is a plot of the longitudinal magnetic flux density along the central axis of the 14 magnet coils arranged as shown in FIGS. 1 to 3, with the operating parameters in Tables 1 and 2. The top plot represents the data in Table 1, whereas the bottom plot represents the data in Table 2.

It is preferred that the linear accelerator is located in the region between 75 and 115 cm from the magnet isocenter, and thus sees a magnetic flux density that ranges from between these values. (a) 18 AWG copper wire; ~0.225 T (target end) to ~0.12 T (gun end); and (b) 8 AWG copper wire 0.11 T (target end) to 0.145 T (gun end). At these field strengths, focusing of the electron beam within the linear accelerator is excellent. This focusing will allow exceptional performance of the linear accelerator.

While the above has provided embodiments having particular parameters, it will be understood that the magnet coils can be configured in a variety of manners. For example, those skilled in the art will recognize that there are many other coil turn and currant combinations that can produce an acceptably homogeneous magnetic field over different imaging volumes and shapes. For example, according to an alternative embodiment where magnetic fields larger than 0.2 T are desired, the coils 20 could be cooled to superconducting temperatures using a cryogenic coolant, and thus superconducting coils can also be used. In such an embodiment, magnetic flux densities on the order of 1 T or higher could be generated while positioning the linear accelerator 14 as has been described above, without adversely affecting the operation of the linear accelerator 14 due to its advantageous positioning. The degree of homogeneity (80 ppm of non-homogeneity or less) is sufficient for many MRI imaging applications, and the 30 centimeters imaging volume is large enough to be useful in image guided radiotherapy.

For the configurations described above, power supplies and cooling systems that are stable enough to be useful in MRI are available commercially (Danfysic, Copenhagen, Denmark).

In the configurations summarized in Tables 1 and 2, a resistive coil was used.

As would be recognized, The MRI assembly shown in FIGS. 1 to 3 does not have any active coils to limit the extent of the fringe magnetic field lines. This is not optimal in MRI since magnetic field lines that go far from the magnet isocentre present a safety hazard, and are thus undesirable. It is typical to use active shielding methods to limit the extent of the MRI $B_0$ field. Although the example of the integrated MRI magnet and linear accelerator shown in FIGS. 1 to 3 does not include active shielding, those skilled in the art will recognize that active shielding techniques can still be used while keeping the radial component of the magnetic field to zero on the central axis of the magnets assembly. This is consistent with the present disclosure, and this will not prevent the functionality of this disclosure.

Those skilled in the art will also recognize that the arrangement shown in FIGS. 1 to 3 is only one of several arrangements that are possible where a linear accelerator can be integrated with an MRI magnet assembly where the long axis of the linear accelerator is in a direction parallel to the $B_0$ field of the MRI. Other embodiments may also utilize noncircular current carrying coils or permanent magnets.

Although embodiments have been described, those of skill in the art will appreciate that variations and modifications may be made without departing from the purpose and scope thereof as defined by the appended claims.

What is claimed is:

1. A radiation therapy system comprising:
   a magnetic resonance imaging (MRI) apparatus configured to generate an MRI magnetic field, the MRI apparatus comprising at least a first magnet and a second magnet spaced apart to define a first gap there between, wherein the first magnet includes an opening therein having a central axis, and wherein the first magnet and the second magnet are co-axially aligned along the central axis so that the central axis extends from the first magnet to the second magnet; and
   a linear accelerator configured to generate a beam of radiation, the linear accelerator coupled to the MRI apparatus so that an axis of particle travel in an accelerating waveguide of the linear accelerator is co-axially aligned with the central axis and configured to expose particles being accelerated therein to the MRI magnetic field so that magnetic force directs the particles along the axis of particle travel.

2. The radiation therapy system of claim 1, wherein the particles are electrons.

3. The radiation therapy system of claim 1, wherein at least a portion of the linear accelerator protrudes through the opening in the first magnet.

4. The radiation therapy system of claim 1, wherein the first magnet comprises a first set of coils and the second magnet comprises a second set of coils, each of the first and second set of coils comprising concentric coils co-axial about the central axis.

5. The radiation therapy system of claim 4 wherein each of the concentric coils is separated by a second gap.

6. The radiation therapy system of claim 4 further comprising two plates in the first gap, each of the plates configured to anchor a corresponding one of the first and second set of coils.

7. The radiation therapy system of claim 4, wherein the first set of coils and the second set of coils comprise copper coils.

8. The radiation therapy system of claim 4, wherein the first set of coils and the second set of coils comprise superconducting coils.

9. The radiation therapy system of claim 1, wherein the first magnet and the second magnet comprise permanent magnets.

10. The radiation therapy system of claim 1, wherein the first magnet and the second magnet comprise non-circular current carrying coils.

11. The radiation therapy system of claim 1, wherein the linear accelerator is located in a region between 75 cm and 115 cm from a magnet isocenter of the MRI apparatus.

12. The radiation therapy system of claim 1, further comprising a rotary joint configured to provide coupling to a linear accelerator RF power supply that is located remote from the radiation therapy system.

* * * * *